Figure 1:
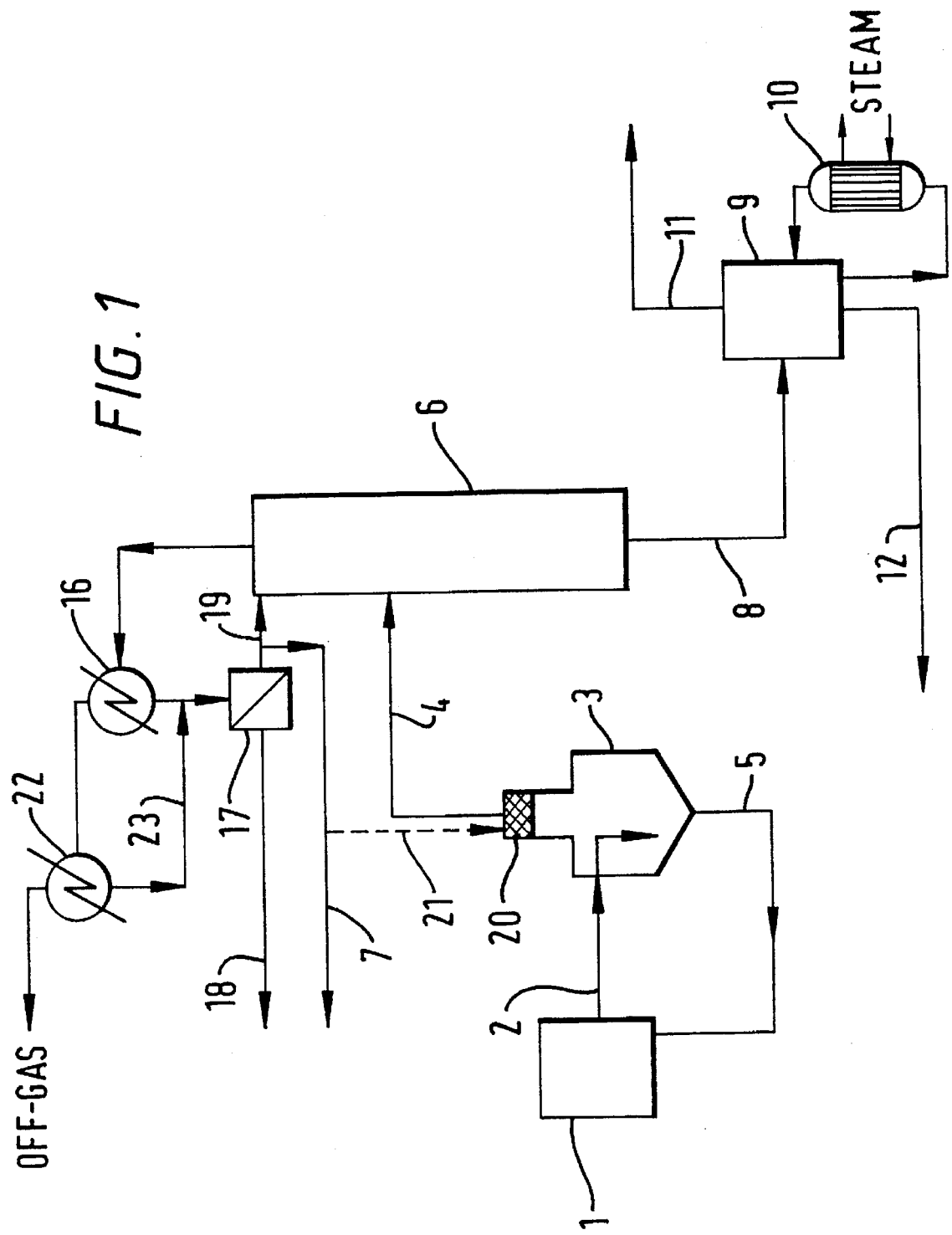

United States Patent [19]

Morris et al.

[11] Patent Number: 5,663,430

[45] Date of Patent: Sep. 2, 1997

[54] PROCESS FOR PURIFYING A CARBOXYLIC ACID

[75] Inventors: George Ernest Morris, Richmond; Stephen James Smith; John Glenn Sunley, both of Cottingham; Robert John Watt, Twickenham; Bruce Leo Williams, Elloughton Brough, all of England

[73] Assignee: BP Chemicals Limited, London, England

[21] Appl. No.: 460,537

[22] Filed: Jun. 2, 1995

[30] Foreign Application Priority Data

Feb. 21, 1995 [GB] United Kingdom ............ 9503385

[51] Int. Cl.$^6$ ................... C07C 51/42; C07C 53/08; C07C 53/10
[52] U.S. Cl. ............... 562/608; 562/606; 562/607; 562/519
[58] Field of Search ................. 562/608, 606, 562/607, 519

[56] References Cited

U.S. PATENT DOCUMENTS

| | | | |
|---|---|---|---|
| 3,772,380 | 11/1973 | Paulik et al. | 260/488 |
| 4,102,921 | 7/1978 | Bartish | 260/532 |
| 4,847,406 | 7/1989 | Steinmetz et al. | 560/80 |

FOREIGN PATENT DOCUMENTS

| | | |
|---|---|---|
| 0350635 | 1/1990 | Australia . |
| 0441260 | 8/1991 | European Pat. Off. . |
| 0497521 | 8/1992 | European Pat. Off. . |
| 0506240 | 9/1992 | European Pat. Off. . |
| 0535825 | 4/1993 | European Pat. Off. . |
| 0573189 | 12/1993 | European Pat. Off. . |
| 0616997 | 9/1994 | European Pat. Off. . |
| 0618183 | 10/1994 | European Pat. Off. . |
| 0618184 | 10/1994 | European Pat. Off. . |
| 0643034 | 3/1995 | European Pat. Off. . |
| 0677505 | 10/1995 | European Pat. Off. . |
| 1767150 | 5/1972 | Germany . |
| 63-91337 | 4/1988 | Japan . |
| 9527899 | 1/1995 | Japan . |
| 1234641 | 6/1971 | United Kingdom . |
| 1234642 | 6/1971 | United Kingdom . |
| 1276326 | 6/1972 | United Kingdom . |

*Primary Examiner*—José G. Dees
*Assistant Examiner*—Rosalynd Williams
*Attorney, Agent, or Firm*—Brooks Haidt Haffner & Delahunty

[57] ABSTRACT

In a process for purifying a carboxylic acid fraction obtained by liquid phase carbonylation of an alkyl alcohol and/or its reactive derivative in which volatile iridium- and/or volatile co-promoter contaminants are converted to involatile forms by contacting with an iodide in the absence of carbon monoxide or at a partial pressure less than that of the carbonylation reaction. The involatile contaminants are then separated from the carboxylic acid.

11 Claims, 2 Drawing Sheets

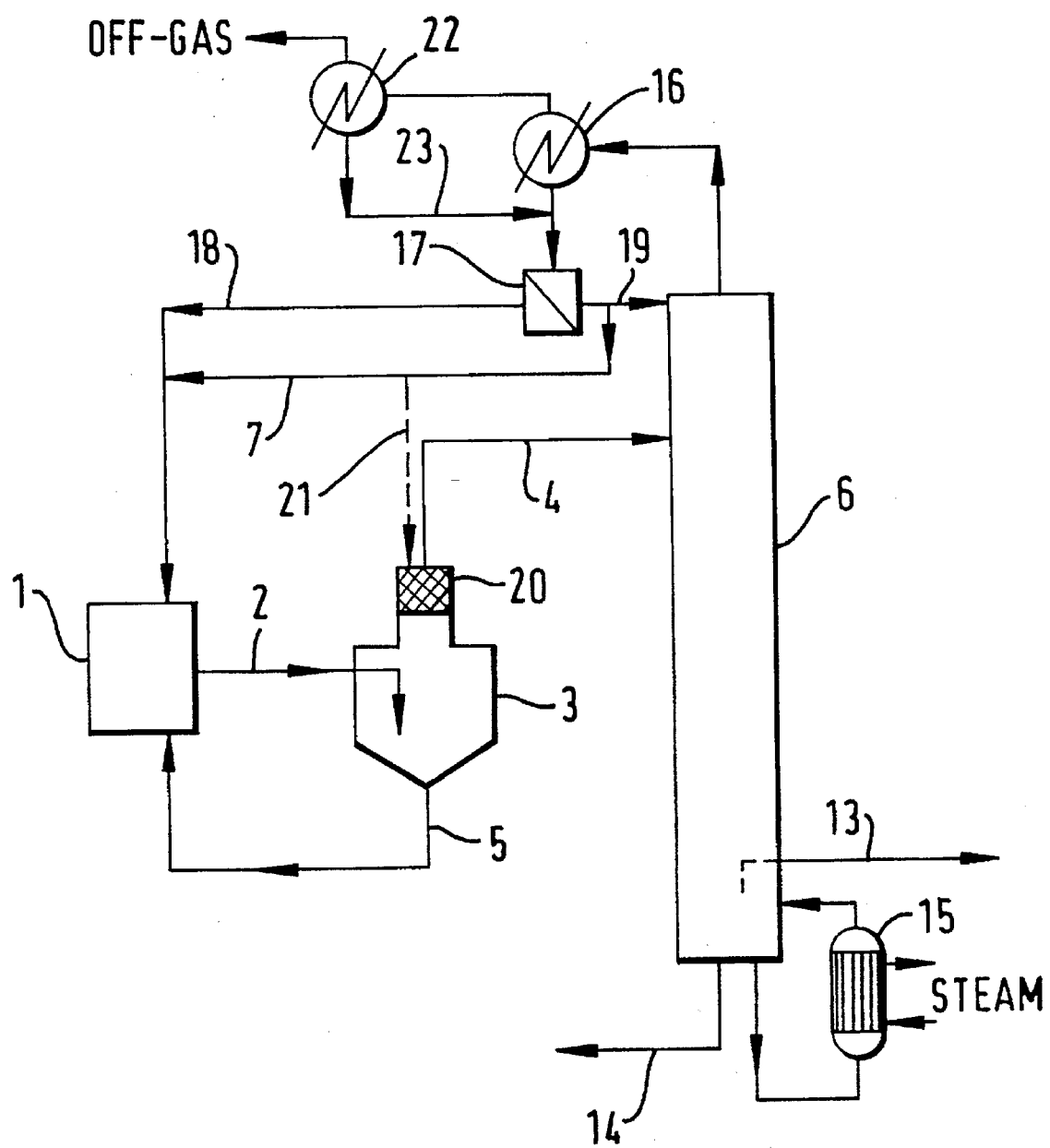

PROCESS FOR PURIFYING A CARBOXYLIC ACID

The present invention relates to a process for purifying a carboxylic acid produced by liquid phase carbonylation of an alkyl alcohol and/or a reactive derivative thereof in the presence of an iridium and/or rhodium catalyst, an alkyl halide promoter and an optional co-promoter selected from ruthenium, osmium and rhenium.

Carbonylation processes in the presence of iridium catalysts are known and are described, for example, in U.S. Pat. No. 3,772,380, European patent publication number EP 0618184-A, UK patents GB 1276326, GB 1234641 and GB 1234642.

European Patent application number EP-0643034-A published after the priority date of the present invention relates to the use of ruthenium and/or osmium as a co-promoter for the iridium catalysed production of acetic acid by carbonylation of methanol and/or a reactive derivative thereof. It is said that under some conditions small amounts of the iridium catalyst may be volatile and that the presence of at least ruthenium may reduce the volatility of the iridium catalyst.

U.S. Pat. No. 4,102,921 relates to a process for forming carboxylic acids and esters by the carbonylation of alcohols, esters, ethers and organo halides in the presence of a catalyst comprising an iridium compound complexed with a polydentate chelating phosphorous or arsenic ligand. The presence of a chelating phosphorus ligand, as opposed to a monodentate ligand, in the iridium compound is said to reduce the volatility of the iridium compound and thereby reduce the amount of catalyst that must be continuously added to the process for synthesis of carboxylic acids and esters.

European patent publication EP-0616997-A1 describes a process for the recovery of a carbonylation product from a liquid reaction composition of an iridium-catalysed carbonylation reaction which comprises subjecting the composition to a vapourisation with or without the addition of heat to produce vapour and liquid fractions in which the liquid fraction has a water concentration of at least 0.5% by weight to stabilise the iridium catalyst. Several product separation/recovery schemes are described, but the problem of volatile iridium and/or volatile optional co-promoters is not considered.

The co-promoters may also be volatile when used with a rhodium carbonylation catalyst.

The technical problem to be solved therefore, is to provide a process for purifying an iridiumo and/or co-promoter-contaminated carboxylic acid fraction obtained by carbonylation in the presence of an iridium and/or rhodium catalyst, an alkyl halide promoter and an optional co-promoter.

According to the present invention there is provided a process for purifying an iridiumo and/or co-promoter-contaminated carboxylic acid fraction obtained by liquid phase carbonylation with carbon monoxide at elevated pressure, of a carbonylation reactant comprising an alkyl alcohol and/or a reactive derivative thereof in the presence of an iridium and/or rhodium catalyst, an alkyl halide promoter, water and an optional co-promoter selected from the group consisting of ruthenium, osmium and rhenium which process comprises (a) contacting said carboxylic acid fraction contaminated with volatile iridium and/or volatile co-promoter contaminants with an iodide in the absence of carbon monoxide or at a partial pressure of carbon monoxide less than that of the carbonylation reaction for sufficient time to convert the volatile iridium catalyst and/or volatile co-promoter contaminants to an involatile form, and (b) separating the involatile iridium catalyst and/or involatile co-promoter from the carboxylic acid fraction.

Also according to the present invention there is provided a process for production of a carboxylic acid which process comprises: (a) contacting in a reactor, carbon monoxide at elevated pressure with a carbonylation reactant comprising an alkyl alcohol and/or a reactive derivative thereof in a liquid reaction composition in the presence of carboxylic acid carbonylation product, an iridium and/or rhodium catalyst, an alkyl halide promoter, water and an optional co-promoter selected from the group consisting of ruthenium, osmium and rhenium; (b) withdrawing from the reactor, liquid reaction composition comprising a carboxylic acid fraction contaminated with volatile iridium and/or volatile co-promoter contaminants; (c) contacting said contaminated carboxylic acid fraction with an iodide in the absence of carbon monoxide or at a partial pressure of carbon monoxide less than that of the carbonylation reaction for sufficient time to convert the volatile iridium catalyst and/or volatile co-promoter to an involatile form; and (d) separating the involatile iridium catalyst and/or involatile co-promoter from the carboxylic acid fraction.

The process of the present invention solves the technical problem defined above by contacting the volatile iridium contaminant with an iodide in the absence of carbon monoxide or at a partial pressure of carbon monoxide less than that of the carbonylation reaction to convert it into an involatile form which may then be separated from the carboxylic acid fraction and thereby reduce contamination of the carboxylic acid fraction by the iridium contaminant. Also, the process of the present invention may render involatile the volatile optional co-promoter and so reduce contamination of the carboxylic acid fraction by the co-promoter. The co-promoter may be used in the carbonylation process with an iridium and/or rhodium carbonylation catalyst. The rhodium carbonylation catalyst is generally not volatile.

A suitable residence time for the process of the present invention may be from 1 minute to 24 hours, preferably from 1 to 600 minutes. A suitable partial pressure of carbon monoxide for the process of the present invention may be from 0 to 5 bar, preferably less than 0.25 bar. The iodide may be an ionic iodide species such as hydrogen iodide or an iodide salt or may be a neutral iodide species such as an alkyl iodide. Preferably, the iodide is derived from the alkyl halide promoter of the carbonylation reaction. Preferably, water is present, for example at greater than 0.5%, particularly if an alkyl iodide is used. The process of the present invention may be performed as a batch or a continuous process, preferably as a continuous process.

In one embodiment of the present invention, liquid reaction composition comprising carboxylic acid product, alkyl halide promoter, iridium (the majority being involatile but with some in a volatile form) and/or rhodium carbonylation catalyst (involatile) and optional carbonylation co-promoter (the majority being involatile but with some in a volatile form) is withdrawn from a carbonylation reactor, contacted with the iodide in the absence of carbon monoxide or at a partial pressure of carbon monoxide less than that of the carbonylation reaction for sufficient time to convert the volatile iridium catalyst and/or volatile optional carbonylation co-promoter to involatile forms, and the carboxylic acid carbonylation product fraction is separated from the involatile iridium catalyst and/or involatile optional co-promoter.

Preferably, in this embodiment, the volatile iridium catalyst and/or volatile optional co-promoter are contacted with the iodide in the absence of carbon monoxide or at a partial pressure of carbon monoxide less than in the reactor in a flash separation vessel having sufficient residence time to effect, at least in part, the conversion of the volatile iridium catalyst and/or volatile optional co-promoter to involatile forms.

Such a flash separation vessel may be an adiabatic flash vessel or may have additional heating means. In this embodiment, liquid carbonylation reaction composition comprising iridium (majority involatile but with some in a volatile form) and/or rhodium carbonylation catalyst (involatile), alkyl halide promoter, water, carboxylic acid product, and optional co-promoter selected from the group consisting of ruthenium, osmium and rhenium (majority involatile but with some in a volatile form) is fed to the flash vessel and is subjected to a reduced pressure whereby a portion of the liquid composition is vaporised to form a vapour fraction comprising carboxylic acid product which is separated from a liquid fraction comprising involatile iridium and/or rhodium catalyst and/or involatile optional co-promoter. It is particularly preferred that the concentration of water in the liquid fraction comprising involatile iridium catalyst be at least 0.5% by weight. Preferably, the flash vessel is provided with a scrubbing section and wash liquid, through which the vapour fraction passes. Preferably, the scrubbing section is packed with Raschig rings or other suitable packing material. This optional scrubbing section may also reduce the entrainment of iridium and/or rhodium catalyst and optional co-promoter from the flash vessel. Such a wash liquid may be provided from a downstream distillation column for example a water-containing process stream. Such a wash liquid may also comprise carboxylic acid, iridium and/or rhodium catalyst and/or optional co-promoter recovered from downstream purification processes. The liquid fraction comprising involatile iridium and/or rhodium catalyst and/or involatile optional co-promoter may also be recycled to the carbonylation reactor. The vapour fraction comprising carboxylic acid may also comprise alkyl halide promoter, unreacted reactants and water which may be separated from the carboxylic acid product by conventional means such as distillation and recycled to the carbonylation reaction. The volatile iridium and/or volatile co-promoter contaminants are contacted with iodide in the flash vessel in the absence of carbon monoxide or at a partial pressure of carbon monoxide less than that of the carbonylation reactor. The iodide may be present in the liquid reaction composition fed to the flash vessel and/or in the optional wash liquid and/or may be generated from alkyl haldie promoter in situ.

In a preferred embodiment of the present invention, liquid carbonylation reaction composition comprising iridium (the majority being involatile but with some in a volatile form) and/or rhodium (involatile) carbonylation catalyst, optional co-promoter (the majority being involatile but with some in a volatile form), carbonylation reactant, water, alkyl halide promoter and carboxylic acid product is fed to a flash separation vessel wherein a liquid fraction comprising the majority of the iridium catalyst and/or rhodium catalyst and the majority of the optional co-promoter is separated from a vapour fraction comprising carboxylic acid, carbonylation reactant, water, alkyl halide carbonylation promoter, volatile iridium contaminant and/or volatile optional co-promoter contaminant; the liquid fraction being recycled to the carbonylation reaction and the vapour fraction being passed to a distillation column wherein the volatile iridium and/or volatile optional co-promoter contaminants are contacted with iodide in the absence of carbon monoxide or at a partial pressure of carbon monoxide less than that of the carbonylation reaction, to convert them into involatile forms. In this embodiment, the distillation column has the advantage of providing a residence time with the iodide greater than may be achieved with just the flash separation vessel and optional scrubbing section. The iodide may be present in the vapour fraction and/or other recycle streams introduced to the distillation column and/or may be generated in situ from alkyl halide promoter. In this embodiment, the flash separation vessel may also be provided with a source of iodide and sufficient residence time to function in part as hereinbeforedescribed to convert volatile iridium and/or volatile optional co-promoter contaminants to involatile forms according to the process of the present invention. In the distillation column an overhead fraction comprising carbonylation reactant and alkyl halide together with some water, acid and ester derivative is separated from one or more bottoms fraction comprising the involatile iridium and/or involatile optional co-promoter and carboxylic acid. The overhead fraction may be recycled to the carbonylation reaction. In this embodiment, the involatile iridium and/or involatile optional co-promoter are separated from the carboxylic acid by removing from the distillation column one or more liquid bottom fractions and passing them to a vaporiser, in which involatile iridium and/or involatile optional co-promoter are separated in a liquid fraction from the carboxylic acid in a vapour fraction. The vapour fraction from the vaporiser comprises carboxylic acid having reduced iridium and/or optional co-promoter contamination compared to that of the feed to the vaporiser. Preferably, such a vaporiser is operated as a flash vaporiser without fractionation. Preferably, methods known in the art are used to prevent entrainment of involatile iridium and/or involatile optional co-promoter for example, by passing the vapour fraction through a small section packed with a suitable packing material. The temperature, pressure and other operating parameters of the vaporiser, such as ratio of liquid to vapour fractions and residence time will depend upon such parameters as the composition, temperature, pressure and flow rate of the carboxylic acid fraction and involatile iridium and/or optional co-promoter contaminant fed to the vaporiser. Suitably, the vaporiser may be operated at a pressure of up to 3 barg, preferably in the range 0 to 2.0 barg. Preferably, the vaporiser is operated at a temperature in the range 90° to 160° C., preferably 100° to 140° C. Suitably, the vaporiser may be operated with a mass ratio of vapour fraction to liquid fraction in the range 500:1 to 10:1, preferably 200:1 to 20:1. Suitably, the residence time of liquid in the vaporiser, calculated as the mass of liquid in the vaporiser divided by the liquid fraction flow rate, may be up to 24 hours, preferably in the range 1 to 600 minutes. Heat may be supplied to the vaporiser by means of a heat exchanger such as a thermosyphon reboiler. Preferably, heat is supplied to the vaporiser by feeding steam or a suitable process stream to the heat exchanger. The steam or process stream may be fed to the heat exchanger at atmospheric, elevated or sub-atmospheric pressure. The process stream used to supply heat may be a vapour and/or a hot liquid. The feed to the vaporiser in this embodiment may comprise independently: (a) iridium and/or optional co-promoter each at a concentration in the range 0.1 to 20 ppm, preferably, 0.1 to 5 ppm; (b) alkyl halide in the range 0.01 to 10% by weight, preferably 0.01 to 5% by weight; (c) carbonylation reactant and/or its ester derivative in the range 0.1 to 30% by weight preferably in the range 0.1 to 15% by weight and (d) water of at least 0.5% by weight. It is particularly preferred that the concentration of water in the liquid fractions from the vaporiser and the flash separation vessel comprising involatile iridium catalyst be at least 0.5% by weight. Preferably, the concentrations of each of the iridium and optional co-promoters in the carboxylic acid vapour fraction separated from the liquid fraction in the vaporiser are independently less than 10% of the iridium and optional co-promoter in the feed to the vaporiser, preferably less than 5%.

In a further embodiment of the present invention, liquid carbonylation reaction composition comprising iridium (the majority being involatile but with some in a volatile form) and/or rhodium (involatile) carbonylation catalyst, optional co-promoter (the majority being involatile but with some in a volatile form), carbonylation reactant, water, alkyl halide promoter and carboxylic acid product is fed to a flash separation vessel wherein a liquid fraction comprising rhodium catalyst and/or the majority of the iridium catalyst and the majority of optional co-promoter is separated from a vapour fraction comprising carboxylic acid, carbonylation reactant, water, alkyl halide carbonylation promoter, volatile iridium contaminant and/or volatile optional co-promoter contaminant; the liquid fraction being recycled to the carbonylation reaction and the vapour fraction being passed to a distillation column wherein the volatile iridium and/or volatile optional co-promoter contaminants are contacted with an iodide in the absence of carbon monoxide or at a partial pressure of carbon monoxide less than that of the carbonylation reaction, to convert them into involatile forms. In this embodiment, the flash separation vessel may also be provided with a source of iodide and sufficient residence time to function in part as hereinbeforedescribed to convert volatile iridium and/or volatile optional co-promoter contaminants to involatile forms according to the process of the present invention. In the distillation column an overhead fraction comprising carbonylation reactant and alkyl halide is separated from one or more bottom fractions comprising the involatile iridium and/or involatile optional co-promoter and carboxylic acid. In this embodiment, the involatile iridium and/or involatile optional co-promoter are separated from the carboxylic acid by taking the carboxylic acid as a vapour fraction from the distillation column and the involatile iridium and/or involatile optional co-promoter in a liquid base bleed stream. Thus, in this embodiment, the vaporiser is integral with the distillation column and vaporisation is effected by the distillation column reboiler rather than by means of a separate heat source. Thus, in this embodiment an overhead fraction comprising reactant and alkyl halide together with some acid, water and ester derivative is removed from the distillation column. The overhead fraction may be recycled to the carbonylation reaction. A vapour fraction comprising carboxylic acid having reduced iridium and/or optional co-promoter contamination compared to that of the feed to the distillation column is taken from near the base of the column. A liquid fraction comprising involatile iridium and/or involatile optional co-promoter is removed separately from the base of the distillation column. In this embodiment, the vapour fraction may be removed immediately above the liquid in the base of the distillation column or may be removed about one or two trays from the base of the distillation column to prevent entrainment of liquid fraction. Methods known in the art to reduce entrainment may be used, for example, the vapour fraction may be passed through a small section packed with a suitable packing material. It is particularly preferred that the concentration of water in the liquid fraction from the flash separation vessel and in the distillation column base bleed comprising involatile iridium catalyst be at least 0.5% by weight. Preferably, the concentrations of each of the iridium and optional co-promoter in the carboxylic acid vapour fraction removed from the distillation column are independently less than 10% of the iridium and optional co-promoter in the feed to the distillation column, preferably less than 5%.

The carboxylic acid produced by the process according to the present invention having reduced iridium and/or optional co-promoter contamination may be further purified by conventional processes, for example distillation to remove impurities such as water, unreacted carbonylation reactant and/or ester derivative thereof and higher boiling carboxylic acid by-products and may be treated with ion exchange resins optionally loaded with suitable metals such as silver to remove iodide impurities.

The carboxylic acid may be a $C_2$ to $C_{11}$ carboxylic acid, preferably a $C_2$ to $C_6$ carboxylic acid, more preferably a $C_2$ to $C_3$ carboxylic acid and most preferably is acetic acid.

Suitably, the reactant for the carbonylation reaction may be an alkyl alcohol having one carbon atom less that the carboxylic acid product or may be a reactive derivative of such alcohol. Preferably, the alkyl alcohol carbonylation reactant is a primary or secondary alkyl alcohol, more preferably a primary alcohol. Suitably, the alkyl alcohol has 1 to 10 carbon atoms, preferably, 1 to 5 carbon atoms, more preferably 1 to 2 carbon atoms and is most preferably methanol. Suitable reactive derivatives of the alkyl alcohol include the ester of the alcohol and the carboxylic acid product, for example methyl acetate; the corresponding dialkyl ether, for example dimethyl ether; and the corresponding alkyl halide, for example methyl iodide. A mixture of alkyl alcohol and reactive derivatives thereof may be used as reactants in the process of the present invention for example a mixture of methanol and methyl acetate. Preferably, methanol and/or methyl acetate are used as reactants.

At least some of the alkyl alcohol and/or reactive derivative thereof will be converted to, and hence present as, the corresponding ester with the carboxylic acid product in the liquid carbonylation reaction composition by reaction with the carboxylic acid product or solvent. Preferably, the concentration of alkyl ester in the liquid reaction composition for iridium-catalysed reaction is in the range 1 to 70% by weight, more preferably 2 to 50% by weight, most preferably 3 to 35% by weight. Preferably, the concentration of alkyl ester in the liquid reaction composition for rhodium-catalysed reactions, is in the range 0.1 to 50% by weight, more preferably up to 35% by weight, yet more preferably up to 15% typically up to 5% by weight.

Water may be formed in situ in the liquid reaction composition, for example, by the esterification reaction between alkyl alcohol reactant and carboxylic acid product. Water may be introduced to the carbonylation reactor together with or separately from other components of the liquid reaction composition,. Water may be separated from other components of reaction composition withdrawn from the reactor and may be recycled in controlled amounts to maintain the required concentration of water in the liquid reaction composition. Preferably, the concentration of water in the liquid reaction composition is in the range 0.1 to 20% by weight, more preferably 1 to 15% by weight, yet more preferably 1 to 10% by weight. Preferably, the alkyl halide in the carbonylation reaction has an alkyl moiety corresponding to the alkyl moiety of the alkyl alcohol reactant. Most preferably, the alkyl halide is methyl halide. Preferably, the alkyl halide is an iodide or bromide, most preferably an iodide. Preferably, the concentration of alkyl halide in the liquid carbonylation reaction composition is in the range 1 to 20% by weight, preferably 2 to 15% by weight.

The iridium catalyst in the liquid reaction composition for the carbonylation reaction may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$,$[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction composition for the carbonylation reaction is in the range 100 to 6000 ppm by weight of iridium.

The liquid carbonylation reaction composition may comprise rhodium carbonylation catalyst instead of iridium or in addition thereto. The rhodium catalyst may be added to the liquid reaction composition in any suitable form which dissolves in the liquid reaction composition or is convertible to a soluble form. Examples of suitable rhodium-containing compounds which may be added to the liquid reaction composition include $[Rh(CO)_2Cl]_2$,$[Rh(CO)_2I]_2$, $[Rh(Cod)Cl]_2$, rhodium (III) chloride, rhodium (III) chloridetrihydrate, rhodium (III) bromide, rhodium (III) iodide, rhodium (III) acetate, rhodium dicarbonylacetylacetonate, $RhCl_3(PPh_3)_3$ and $RhI(CO)(PPh_3)_2$. Preferably, the rhodium catalyst concentration in the liquid reaction composition is in the range 50 to 5000 ppm by weight of rhodium, preferably 100 to 1000 ppm.

Preferably, the liquid reaction composition for the carbonylation reaction additionally comprises as co-promoter one or more of osmium, rhenium and ruthenium. The osmium, rhenium or ruthenium promoter may comprise any osmium, rhenium or ruthenium containing compound which is soluble in the liquid reaction composition. The co-promoter may be added to the liquid reaction composition for the carbonylation reaction in any suitable form which dissolves in the liquid reaction composition or is convertible to soluble form. Preferably, the co-promoter compound may be used as chloride free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, $[Ru(CO)_3I_3]^-H^+$, tetra(aceto)chlororuthenium(II, III), ruthenium (III) acetate, ruthenium (III) propionate, ruthenium (III) butyrate, ruthenium pentacarbonyl, triruthieniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1,5-diene) ruthenium (II) polymer and tris(acetylacetonate)ruthenium (III).

Examples of suitable osmium containing compounds which may be used include osmium (III) chloride hydrate and anhydrous, osmium metal, osmium tetraoxide, triosmiumdodecacarbonyl, pentachloro-μ-nitrododiosmium and mixed osmium halocarbonyls such as tricarbonyldichloroosmium (II) dimer and other organoosmium complexes.

Examples of suitable rhenium-containing compounds which may be used include $Re_2(CO)_{10}$, $Re(CO)_5Cl$, $Re(CO)_5Br$, $Re(CO)_5I$, $ReCl_3.xH_2O$ $ReCl_5.yH_2O$ and $[\{Re(CO)_4I\}_2]$.

Preferably, the osmium, rhenium or ruthenium co-promoter is free from alkali and alkaline earth contaminants, such as sodium, when used with an iridium catalyst.

The molar ratio of each co-promoter (when present) to iridium and/or rhodium catalyst in the reaction composition for the carbonylation reaction may suitably be in the range 0.1:1 to 100:1, preferably greater than 0.5:1, more preferably greater than 1:1 and preferably up to 20:1 more preferably up to 15:1 and yet more preferably up to 10:1.

The carbon monoxide reactant for the carbonylation reaction may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the reaction is suitably in the range 1 to 70 bar, preferably 3 to 35 bar and more preferably up to 15 bar.

The pressure of the carbonylation reaction is suitably in the range 15 to 200 barg, preferably 15 to 100 barg, more preferably 20 to 50 barg and yet more preferably up to 35 barg. The temperature of the carbonylation reaction is suitably in the range 100° to 300° C., preferably in the range 160° to 220° C.

Carboxylic acid may be used as a solvent for the carbonylation reaction.

Corrosion metals, particularly nickel, iron, molybdenum and chromium should be kept to a minimum in the liquid reaction composition catalysed by iridium as these may have an adverse effect on the reaction.

In a particularly preferred embodiment, the present invention provides a process for the production of acetic acid which process comprises:

(a) contacting in a reactor, carbon monoxide at elevated partial pressure with methanol and/or a reactive derivative thereof, in a liquid reaction composition in the presence of an iridium and/or rhodium catalyst, methyl iodide and optional co-promoter selected from the group consisting of osmium, rhenium and ruthenium to produce acetic acid;

(b) withdrawing from the reactor, liquid reaction composition comprising iridium and/or rhodium carbonylation catalyst, optional co-promoter, methyl acetate, water, methyl iodide, acetic acid and hydrogen iodide and feeding the liquid reaction composition to a flash separation vessel wherein a liquid fraction comprising the rhodium catalyst and/or the majority of the iridium catalyst and/or the majority of the optional co-promoter and preferably having a water concentration of at least 0.5% by weight if iridium catalyst is present, is separated from a vapour fraction comprising acetic acid, methyl acetate, water, methyl iodide, volatile iridium contaminant and/or volatile optional promoter contaminant; the flash separation vessel having no carbon monoxide or a carbon monoxide partial pressure less than that of the carbonylation reactor and preferably having a scrubbing section and optionally being provided with sufficient residence time and iodide concentration to function at least in part to convert volatile iridium and/or volatile optional co-promoter to involatile forms;

(c) recycling the liquid fraction from step (b) to the carbonylation reactor;

(d) passing the vapour fraction from step (b) to a fractional distillation column wherein volatile iridium contaminant and/or volatile optional co-promoter contaminant in the vapour fraction are contacted with an iodide in the absence of carbon monoxide or at a partial pressure of carbon monoxide less than that of the carbonylation reaction, for sufficient time to convert, them into involatile forms.

(e) removing from the distillation column (i) an overhead fraction comprising methyl acetate, methyl iodide and optionally some water, acetic acid and methanol and (ii) one or more bottom liquid fractions comprising involatile iridium, and involatile optional co-promoter and acetic acid, optionally some methyl acetate and optionally some methyl iodide and preferably if iridium is present having at least 0.5% water; and (f) recycling the overhead fraction from step (e) to the carbonylation reactor;

(g) feeding the one or more bottom liquid fractions from step (e) comprising acetic acid and involatile iridium and/or involatile optional co-promoter to a further flash vaporiser wherein acetic acid having reduced iridium and/or optional co-promoter contamination compared to that of the feed to the vaporiser, is separated as a vapour fraction from a liquid fraction comprising involatile iridium and/or involatile optional co-promoter; and (h) recycling the liquid fraction from step (g) to the carbonylation reactor.

In a modification of this embodiment, the further flash vaporiser may be integral with the fractional distillation column used to effect the fractional distillation step so that steps (e) to (h) are modified to:

(e*) removing from the distillation column (i) an overhead fraction comprising methyl acetate, methyl iodide and optionally some water, acetic acid and methanol; (ii) a vapour fraction comprising acetic acid having reduced iridium and/or optional co-promoter contamination compared to that of the feed to the distillation column; and (iii) a base bleed stream comprising involatile iridium and/or involatile optional co-promoter and preferably having a water concentration of at least 0.5% by weight, if iridium is present; and (f*) recycling the overhead fraction from step (e*) to the carbonylation reactor;

(g*) recycling the base bleed stream from step (e*) to the carbonylation reactor.

As previously described, the base vapour fraction may be withdrawn at about one or two trays from the base of the distillation column to reduce entrainment.

In these embodiments an aqueous phase separated in the distillation column may be used as wash liquid to the preliminary flash vaporiser.

In a suitable process for the production of acetic acid by carbonylation of methanol in step (a) the carbonylation may be performed at 185° to 195° C., typically 189° C. to 190° C.; 22 to 40 barg, typically 27.6 barg pressure with a hydrogen partial pressure of less than 0.5 bar and a reaction composition comprising by weight 500 to 3000 ppm, typically 1000 to 2500 ppm iridium; 500 to 6000 ppm, typically 1000 to 3000 ppm ruthenium; 2 to 20%, typically about 4 to 8% methyl iodide; 1–10%, typically about 4 to 8% water; 5 to 35%, typically about 12% to 18% methyl acetate and the balance acetic acid. The liquid reaction composition may be passed in step (b) to a flash separation vessel operated at up to 3 barg, typically 1.48 barg and having an optional wash liquid and suitable residence time to effect, at least in part, the process of the present invention. The vapour fraction produced therein may be passed in step (d) to tray 3 counted from the base of a 36 tray distillation column having a suitable residence time to effect the process of the present invention. The liquid bottom acid fraction from the distillation column may be passed, in step (g), to a vaporiser in which a vapour acetic acid fraction comprising at least 90% by weight of the feed having reduced iridium and ruthenium contamination is separated from a liquid fraction. The vapour acetic acid fraction from step(g) may be dried in a distillation column to which may be fed methanol to convert hydrogen iodide to methyl iodide which is separated from the acetic acid in the column. A suitable drying column may have about 28 trays with feed at tray 20 from the base and methanol feed at tray 6 numbered from the base. Water, methyl acetate and methyl iodide is taken from the head of the drying column and recycled to the reactor. Dry acetic acid is taken from the base and is then purified of propionic acid in a heavy ends distillation column, for example having 45 trays, to produce saleable acetic acid. In the heavy ends column residual hydrogen iodide may be removed by the addition of potassium acetate and purified acetic acid is taken as a liquid for example from tray 40 of a 45 tray column (numbered from the base) with 10% of the acid as an overhead bleed together with a small bleed of acid from the base of the distillation column. Operating with this process gives acetic acid leaving the base of the drying column with very low levels of higher organic iodides and other iodide species. As a result acetic acid can be obtained from the heavy ends column containing less than 20 ppb, preferably less than 8 ppb and more preferably less than 5 ppb total iodides which is saleable without further purification.

The invention will now be illustrated by reference to the following Examples and by reference to FIGS. 1 and 2 in which FIG. 1 is a simplified flow diagram of the relevant part of the apparatus for the process for the manufacture of acetic acid from methanol and/or a reactive derivative thereof and FIG. 2 is a modification of the apparatus of FIG. 1 with the vaporiser being integral with the distillation column.

Referring to FIGS. 1 and 2, in use the liquid reaction composition comprising acetic acid, water, unreacted methanol and/or a reactive derivative thereof, iridium catalyst, methyl iodide and optional co-promoter selected from osmium, rhenium and ruthenium is passed from the carbonylation reactor 1 by line 2 to the flash separation vessel 3. A vapour fraction comprising acetic acid, water, methyl iodide, unreacted methanol and/or reactive derivative thereof, volatile iridium contaminant and volatile optional co-promoter contaminant is removed from the flash separation vessel via line 4 and a liquid fraction comprising the majority of the iridium catalyst and optional co-promoter is removed via line 5 and recycled to the carbonylation reactor 1. The vapour fraction from the flash separation vessel is fed via line 4 to a distillation column 6. From the head of the first distillation column is taken an overhead vapour fraction comprising methanol/methyl acetate reactant, methyl iodide, water and some acetic acid. The overhead vapour fraction is cooled by condenser 16 and passed to decanter 17 where it phase separates to give an aqueous phase and a methyl iodide rich phase. The methyl iodide rich phase is recycled to the carbonylation reactor along line 18. A portion of the aqueous phase is returned to the first distillation column as reflux along line 19, the remainder being recycled to the reactor along line 7. Further vapours may be condensed from the vapour from condenser 16 by optional second condenser 22 and returned to the decanter along line 23. In the distillation column, volatile iridium and volatile optional co-promoter are contacted with iodide derived from the alkyl iodide in the feed to the column at a partial pressure of carbon monoxide less than that of the carbonylation reactor, for sufficient time to convert the iridium and optional co-promoter to involatile forms.

In FIG. 1, a liquid fraction consisting of predominantly iridium- and optional co-promoter-contaminated acetic acid is withdrawn from the bottom of the distillation column and is fed via line 8 to a further flash vaporiser 9. The further flash vaporiser is heated by means of an external thermosyphon reboiler 10. A vapour fraction of acetic acid having substantially reduced iridium and optional co-promoter contamination is taken from the further flash vaporiser 9 via line 11 and may be further purified by conventional means such as distillation (not shown) to remove water, methanol, methyl iodide, methyl acetate, and propionic acid. A liquid fraction is taken from the further vaporiser via line 12 and recycled to the reactor 1.

FIG. 2 shows a modification of the apparatus of FIG. 1 in that the further flash vaporiser is integral with the distillation column, the remaining apparatus being the same. From the base of the distillation column is taken via line 13 a vapour base fraction comprising acetic acid having a reduced iridium and optional co-promoter content than if a liquid fraction were taken as a liquid from the base of the distillation column. A liquid bleed fraction is also taken from the base of the distillation column and is recycled to the reactor via line 14. The vapour fraction may be removed about one or two trays from the base of the distillation column. The vapour fraction may be further purified by conventional means such as distillation (not shown) to remove water, methyl iodide, methyl acetate, methanol and propionic acid.

In FIGS. 1 and 2 the flash separation vessel is also provided with a scrubbing section 20 with optional liquid wash through line 21. This wash may be provided at least in part from the aqueous phase of the distillation column overhead decanter (from line 7). The residence time within the flash separation vessel may be sufficient to effect, at least in part, some conversion of the volatile iridium and volatile optional co-promoter to involatile forms.

EXAMPLE 1

Using apparatus similar to that shown in FIG. 1 but with an electrically heated vaporiser methanol was carbonylated in the reactor 1 at 190.0° C. and a total pressure of 27.6 barg. The liquid reaction composition comprised water, methyl iodide, methyl acetate, iridium catalyst at 2250 ppm and ruthenium promoter at 2300 ppm. The calculated carbon monoxide partial pressure in the reactor was 8.2 bara and the calculated hydrogen partial pressure was 0.35 bara based on analysis of the combined off-gas streams (high and low pressure) vented from the system. Liquid reaction composition was withdrawn from the reactor and passed to the flash separation vessel 3 operated at a pressure of 1.48 barg. Vapour fraction from the flash separation vessel comprising water, methyl iodide, methyl acetate, acetic acid, 0.38 ppm iridium and 0.73 ppm ruthenium at an estimated flow rate of 9.0 kg/hr was passed along line 4 to the distillation column 6 operated with a reboiler temperature of 136.4° C., a reboiler pressure of 1.46 barg and a residence time for the catalyst/co-promoter in the reboiler of 0.6 hours. In the distillation column volatile iridium catalyst and volatile ruthenium co-promoter were contacted with iodide derived from the methyl iodide in the feed at a partial pressure of carbon monoxide less than that in the carbonylation reactor for a residence time sufficient to convert the volatile catalyst and volatile, co-promoter to involatile forms. The organic phase in the distillation column decanter comprising 29.3% by weight methyl iodide, 53.1% by weight methyl acetate, and lesser amounts of water and acetic acid, comprised 0.04 ppm iridium and 0.13 ppm ruthenium and was recycled to the reactor at a flow rate of 4.8 kg/hr. The aqueous phase in the decanter of the distillation column comprising 68% by weight water together with lesser amounts of methyl iodide, methyl acetate and acetic acid comprised 0.35 ppm iridium and 0.10 ppm ruthenium. Reflux rate of the aqueous phase to the distillation column was 1.5 kg/hr and recycle rate to the reactor was 0.15 kg/hr.

A liquid fraction comprising 0.75 ppm iridium and 1.25 ppm ruthenium was removed from the bottom of the distillation column at a rate of 4.3 kg/hr and fed to vaporiser 9.

The vaporiser was operated at a temperature of 111.4° C., a pressure of 0.0 barg with a residence time of 5.5 hours. In the vaporiser, a vapour fraction comprising 84.1% by weight acetic acid, 0.1% by weight methyl iodide, 5.1% by weight methyl acetate, 9.4% by weight water, 0.0005 ppm iridium and 0.001 ppm ruthenium was separated at a rate of 4.2 kg/hr from a liquid fraction comprising 36.8 ppm iridium and 59.0 ppm ruthenium removed at a rate of 90 g/hr.

Mass accountabilities of iridium and ruthenium in the distillation column were 101% and 96% respectively and in the vaporiser were 102% and 98% respectively. The acetic acid vapour fraction from the vaporiser comprised approximately 0.06% of the iridium and approximately 0.06% of the ruthenium fed to the distillation column. The acetic acid may be dried in a distillation column with methanol feed to remove hydrogen iodide and purified of propionic acid in a heavy ends column with potassium acetate addition to remove residual hydrogen iodide to produce saleable acetic acid having less than 20 ppb total iodide.

EXAMPLE 2

Using apparatus similar to that shown in FIG. 2 but with an electrically heated reboiler, methanol was carbonylated in the reactor 1 at 189.7° C. and a total pressure of 27.6 barg. The liquid reaction composition comprised water, methyl iodide, methyl acetate, iridium catalyst at 2200 ppm and ruthenium promoter at 2530 ppm. The calculated carbon monoxide partial pressure in the reactor was 8.1 bara and the calculated hydrogen partial pressure was 0.37 bara based on analysis of the combined off-gas streams (high and low pressure) vented from the system. Liquid reaction composition was withdrawn from the reactor and passed to the flash separation vessel 3 operated at a pressure of 1.48 barg. Vapour fraction from the flash separation vessel comprising water, methyl iodide, methyl acetate, acetic acid, 0.3 ppm iridium and 0.54 ppm ruthenium at an estimated flow rate of 9.3 kg/hr Was passed along line 4 to the distillation column 6 operated with a reboiler temperature of 145.6° C., a reboiler pressure of 1.46 barg and a residence time for the catalyst/co-promoter in the reboiler of 20 hours. In the distillation column volatile iridium catalyst and volatile ruthenium co-promoter were contacted with iodide derived from the methyl iodide in the feed at a partial pressure of carbon monoxide less than that in the carbonylation reactor for a residence time sufficient to convert the catalyst and co-promoter to involatile forms. The organic phase in the distillation column decanter comprising 29.2% by weight methyl iodide, 55.3% by weight methyl acetate, and lesser amounts of water and acetic acid, comprised 0.06 ppm iridium and 0.07 ppm ruthenium and was recycled to the reactor at a flow rate of 3.9 kg/hr. The aqueous phase in the decanter of the distillation column comprising 67.2% by weight water together with lesser amounts of methyl iodide, methyl acetate and acetic acid comprised 0.02 ppm iridium and 0.01 ppm ruthenium. Reflux rate of the aqueous phase to the distillation column was 1.5 kg/hr and recycle rate to the reactor was 0.18 kg/hr.

A base acetic acid vapour fraction comprising 81.1% by weight acetic acid, 0.3% by weight methyl iodide, 5.6% by weight methyl acetate, 9.3% by weight water, 0.0005 ppm iridium and 0.001 ppm ruthenium was removed via line 13 at a rate of 4.5 kg/hr. The acetic acid may be dried in a distillation column with methanol feed to remove hydrogen iodide and purified of propionic acid in a heavy ends column with potassium acetate addition to remove residual hydrogen iodide to produce saleable acetic acid having less than 20 ppb total iodide.

A bottom liquid fraction comprising 22 ppm iridium and 40 ppm ruthenium was removed from the bottom of the distillation column at a rate 120 g/hr.

Mass accountabilities of iridium and ruthenium in the distillation column were 103% and 101% respectively. The acetic acid vapor fraction from the vaporiser comprised approximately 0.08% of the iridium and approximately 0.09% of the ruthenium fed to the distillation column.

We claim:

1. A process for purifying an iridium- and/or co-promoter-contaminated carboxylic acid fraction obtained by liquid phase carbonylation with carbon monoxide at elevated pressure, of a carbonylation reactant comprising an alkyl alcohol and/or a reactive derivative thereof in the presence of an iridium and/or rhodium catalyst, an alkyl halide promoter, water and an optional co-promoter selected from the group consisting of ruthenium, osmium and rhenium which process comprises:

(a) contacting said carboxylic acid fraction contaminated with volatile iridium and/or volatile co-promoter contaminants with an iodide in the absence of carbon monoxide or at a partial pressure of carbon monoxide less than that of the carbonylation reaction for sufficient time to convert the volatile iridium catalyst and/or volatile co-promoter contaminants to an involatile form, and (b) separating the involatile iridium catalyst and/or involatile co-promoter from the carboxylic acid fraction.

2. A process for production of a carboxylic acid which process comprises:

(a) contacting in a reactor, carbon monoxide at elevated pressure with a carbonylation reactant comprising an alkyl alcohol and/or a reactive derivative thereof in a liquid reaction composition in the presence of carboxylic acid carbonylation product, an iridium and/or rhodium catalyst, alkyl halide promoter, water and an optional co-promoter selected from the group consisting of ruthenium, osmium and rhenium; (b) withdrawing from the reactor, liquid reaction composition comprising a carboxylic acid fraction contaminated with volatile iridium and/or volatile co-promoter contaminants (c) contacting said contaminated carboxylic acid fraction with an iodide in the absence of carbon monoxide or at a partial pressure of carbon monoxide less than that of the carbonylation reaction for sufficient time to convert the volatile iridium catalyst and/or volatile co-promoter to an involatile form; and (d) separating the involatile iridium catalyst and/or involatile co-promoter from the carboxylic acid fraction.

3. A process as claimed in claim 2 in which the iodide is derived from the alkyl halide promoter of the carbonylation reaction.

4. A process as claimed in claim 3 in which liquid carbonylation reaction composition comprising iridium and/or rhodium carbonylation catalyst, alkyl halide promoter, water, carboxylic acid product and optional co-promoter selected from the group consisting of ruthenium, osmium and rhenium is fed to a flash separation vessel wherein the volatile iridium catalyst and/or volatile optional co-promoter are contacted with the iodide in the absence of carbon monoxide or at a partial pressure of carbon monoxide less than in the reactor, the flash separation vessel having sufficient residence time to effect at least in part, the conversion of the volatile iridium catalyst and/or volatile optional co-promoter to involatile forms, and is subjected to a reduced pressure therein whereby a portion of the liquid composition is vaporised to form a vapour fraction comprising carboxylic acid product which is separated from a liquid fraction comprising involatile iridium and/or rhodium catalyst and/or involatile optional co-promoter.

5. A process as claimed in claim 4 in which the flash vessel is provided with a scrubbing section and wash liquid, through which the vapour fraction passes.

6. A process as claimed in claim 2 in which liquid carbonylation reaction composition comprising iridium and/or rhodium carbonylation catalyst, optional co-promoter, carbonylation reactant, water, alkyl halide promoter, and carboxylic acid product is fed to a flash separation vessel wherein a liquid fraction comprising rhodium catalyst and/or the majority of the iridium catalyst and the majority of the optional co-promoter is separated from a vapour fraction comprising carboxylic acid, carbonylation reactant, water, alkyl halide carbonylation promoter, volatile iridium contaminant and/or volatile optional co-promoter contaminant; the liquid fraction being recycled to the carbonylation reaction and the vapour fraction being passed to a distillation column wherein the volatile iridium and/or volatile optional co-promotor contaminants are contacted with iodide in the absence of carbon monoxide or at a partial pressure of carbon monoxide less than that of the carbonylation reaction, to convert them into involatile forms and wherein an overhead fraction comprising carbonylation reactant and alkyl halide together with some water, acid and ester derivative is separated from one or more bottoms fraction comprising the involatile iridium and/or involatile optional co-promoter and carboxylic acid.

7. A process as claimed in claim 6 in which one or more liquid bottom fractions comprising involatile iridium and/or involatile optional co-promoter and carboxylic acid are removed from the distillation column and passed to a vaporiser in which the involatile iridium and/or involatile optional co-promoter are separated in a liquid fraction from the carboxylic acid in a vapour fraction.

8. A process as claimed in claim 6 in which a vapour fraction comprising carboxylic acid having reduced iridium and/or optional co-promoter contamination compared to that of the feed to the distillation column is taken from the distillation column and a liquid stream comprising involatile iridium and/or involatile optional co-promoter is taken as a base bleed stream from the column.

9. A process as claimed in any one of claims 6 to 8 in which the flash separation vessel is provided with a residence time, and iodide in the absence of carbon monoxide or at a partial pressure of carbon monoxide less than in the reactor sufficient to effect at least in part conversion of volatile iridium and/or volatile optional copromoter to involatile forms.

10. A process for the production of acetic acid which process comprises:

(a) contacting in a reactor, carbon monoxide at elevated partial pressure with methanol and/or a reactive derivative thereof, in a liquid reaction composition in the presence of an iridium and/or rhodium catalyst, methyl iodide and optional co-promoter selected from the group consisting of osmium, rhenium and ruthenium to produce acetic acid;

(b) withdrawing from the reactor, liquid reaction composition comprising iridium and/or rhodium carbonylation catalyst, optional co-promoter, methyl acetate, water, methyl iodide, acetic acid and hydrogen iodide and feeding the liquid reaction composition to a flash separation vessel wherein a liquid fraction comprising the rhodium catalyst and/or the majority of the iridium catalyst and/or the majority of the optional co-promoter and preferably having a water concentration of at least 0.5% by weight if iridium catalyst is present, is separated from a vapour fraction comprising acetic acid, methyl acetate, water, methyl iodide, volatile iridium contaminant and/or volatile optional promoter contaminant; the flash separation vessel having no carbon monoxide or a carbon monoxide partial pressure less than that of the carbonylation reactor and preferably having a scrubbing section and optionally being provided with sufficient residence time and iodide concentration to function at least in part to convert the volatile iridium and/or volatile optional co-promoter to involatile forms;

(c) recycling the liquid fraction from step (b) to the carbonylation reactor;

(d) passing the vapour fraction from step (b) to a fractional distillation column wherein the volatile iridium contaminant and/or volatile optional co-promoter contaminant in the vapour fraction are contacted with an iodide in the absence of carbon monoxide or at a partial pressure of carbon monoxide less than that of the carbonylation reaction, for sufficient time to convert them into involatile forms;

(e) removing from the distillation column (i) an overhead fraction comprising methyl acetate, methyl iodide and optionally some water, acetic acid and methanol and (ii) one or more bottom liquid fractions comprising involatile iridium and involatile optional co-promoter and acetic acid and preferably at at least 0.5% water if iridium is present; and (f) recycling the overhead fraction from step (e) to the carbonylation reactor;

(g) feeding the one or more bottom liquid fractions from step (e) comprising acetic acid and involatile iridium and/or involatile optional co-promoter to a further flash vaporiser wherein acetic acid having reduced iridium and/or optional co-promoter contamination compared to that of the feed to the vaporiser, is separated as a vapour fraction from a liquid fraction comprising involatile iridium and/or involatile optional co-promoter; and (h) recycling the liquid fraction from step (g) to the carbonylation reactor.

11. A process as claimed in claim 10 modified in that steps (e) to (h) are modified to:

(e*) removing from the distillation column (i) an overhead fraction comprising methyl acetate, methyl iodide and optionally some water, acetic acid and methanol; (ii) a vapour fraction comprising acetic acid having reduced iridium and/or optional co-promoter contamination compared to that of the feed to the distillation column; and (iii) a base bleed stream comprising involatile iridium and/or involatile optional co-promoter and preferably having a water concentration of at least 0.5% by weight if iridium is present, and (f*) recycling the overhead fraction from step (e*) to the carbonylation reactor; (g*) recycling the base bleed stream from step (e*) to the carbonylation reactor.

* * * * *

UNITED STATES PATENT AND TRADEMARK OFFICE
CERTIFICATE OF CORRECTION

PATENT NO. : 5,663,430
DATED : September 2, 1997
INVENTOR(S) : George E. Morris et al.

It is certified that error appears in the above-identified patent and that said Letters Patent is hereby corrected as shown below:

Column 1,
Line 49, "iridiumo" should read -- iridium --
Line 55, "iridiumo" should read -- iridium --

Column 6,
Line 63, "Preferably, the alkyl" should start a new Paragraph

Column 7,
Line 20, correct the last formula on the line to read -- $IrBr_3.4H_2O$, --

Column 12,
Line 15, delete the comma "," after the word "volatile"

Column 13,
Line 35, insert -- purified -- after "The"

Column 14,
Line 7, there should be a semi-colon -- ; -- after "contaminants" and before "(c)"
Line 52, "co-promotor" should read -- co-promoter --

Signed and Sealed this

Twelfth Day of August, 2003

JAMES E. ROGAN
*Director of the United States Patent and Trademark Office*